United States Patent
Buczynski et al.

(10) Patent No.: US 7,550,122 B2
(45) Date of Patent: Jun. 23, 2009

(54) DECONTAMINATION SYSTEM WITH AIR BYPASS

(75) Inventors: Peter J. Buczynski, Girard, PA (US); Michael A. Bacik, Fairview, PA (US)

(73) Assignee: American Sterilizer Company, Mentor, OH (US)

( * ) Notice: Subject to any disclaimer, the term of this patent is extended or adjusted under 35 U.S.C. 154(b) by 112 days.

(21) Appl. No.: 11/421,265

(22) Filed: May 31, 2006

(65) Prior Publication Data

US 2008/0279719 A1 Nov. 13, 2008

(51) Int. Cl.
*A61L 2/00* (2006.01)
*A61L 9/00* (2006.01)

(52) U.S. Cl. .................. 422/292; 422/28; 422/295; 422/298

(58) Field of Classification Search ............ 422/298, 422/292
See application file for complete search history.

(56) References Cited

U.S. PATENT DOCUMENTS

| | | | | |
|---|---|---|---|---|
| 3,478,900 | A * | 11/1969 | Jeppson | 219/684 |
| 4,336,329 | A * | 6/1982 | Hesse et al. | 435/3 |
| 4,395,831 | A * | 8/1983 | Nielsen | 34/86 |
| 4,869,872 | A | 9/1989 | Baltes | 422/1 |
| 4,898,713 | A * | 2/1990 | Picard | 422/3 |
| 5,730,944 | A * | 3/1998 | Peake | 422/111 |
| 5,872,359 | A | 2/1999 | Stewart et al. | 250/339.12 |
| 6,734,405 | B2 * | 5/2004 | Centanni et al. | 219/628 |
| 2002/0114727 | A1 * | 8/2002 | McVey et al. | 422/4 |
| 2003/0118471 | A1 * | 6/2003 | Howe et al. | 422/26 |
| 2005/0084431 | A1 * | 4/2005 | Hill et al. | 422/305 |
| 2005/0129571 | A1 | 6/2005 | Centanni | 422/31 |
| 2005/0276721 | A1 | 12/2005 | Centanni | 422/28 |

OTHER PUBLICATIONS

"Steris VHP® 1000ED Mobile Biodecontamination System," Low Temperature Biodecontamination, Steris Corporation, Aug. 2005.
"Introducing the Steris VHP® 100 Biodecontamination Systems," Low Temperature Biodecontamination, Steris Corporation, 2002.
"MDS™—Series, Modular Dehumidification System," Munters Product Information, Munters Corporation, Feb. 1999.
"Modular Dehumidification Systems," Dehumidification Division, Munters Corporation, 2000.

* cited by examiner

*Primary Examiner*—E. Leigh McKane
*Assistant Examiner*—Regina Yoo
(74) *Attorney, Agent, or Firm*—Kusner & Jaffe; Michael A. Centanni

(57) ABSTRACT

A decontamination system for decontaminating an enclosure defining a chamber or region. The decontamination system includes an air bypass for introducing atmospheric air into the decontamination system and bypassing air to the atmosphere in response to system operating conditions. The air bypass allows increased airflow through the decontamination system during certain operating modes of the decontamination system (i.e., dehumidification and aeration phases), thereby reducing the amount of time needed to dehumidify and aerate the enclosure. The air bypass also facilitates the use of a high capacity dryer in the decontamination system.

23 Claims, 1 Drawing Sheet

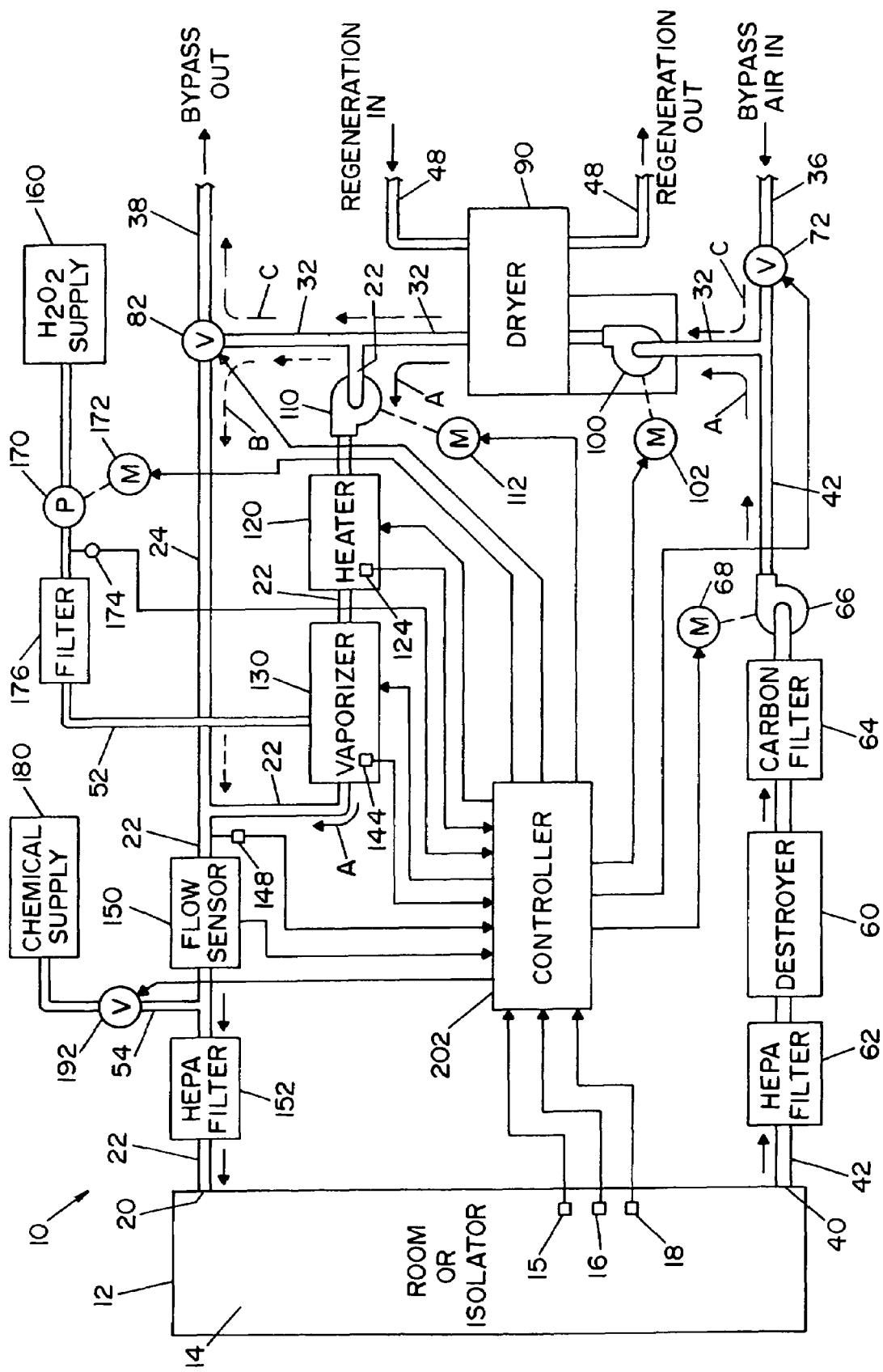

DECONTAMINATION SYSTEM WITH AIR BYPASS

FIELD OF THE INVENTION

The present invention relates generally to the field of decontamination systems that use a decontaminant in its gaseous or vaporous phase, and more particularly to a decontamination system having an air bypass.

BACKGROUND OF THE INVENTION

Decontamination methods are used in a broad range of applications, and have used an equally broad range of decontaminating agents. As used herein the term "decontamination" refers to the inactivation of bio-contamination, and includes, but is not limited to, sterilization and disinfection.

Gaseous and vaporous decontamination systems rely on maintaining certain process parameters in order to achieve a target decontamination assurance level. For hydrogen peroxide vapor decontamination systems, those process parameters include the concentration of the hydrogen peroxide vapor, the degree of saturation, the temperature and pressure, and the exposure time. By controlling these process parameters, the desired decontamination assurance levels can be successfully obtained while avoiding condensation of the hydrogen peroxide due to vapor saturation.

Conventional vaporized hydrogen peroxide (VHP) decontamination systems for decontaminating enclosures (such as rooms or isolators), are generally closed-loop systems that contain a destroyer and a dryer within the system. In such closed-loop systems, a decontaminant is continuously conveyed through the enclosure. Decontaminant exiting the enclosure is directed to the destroyer to break down the vaporized hydrogen peroxide into water and oxygen. This type of arrangement allows the vaporized hydrogen peroxide concentration within the system to be maintained at a desired concentration depending on the airflow and decontaminant (typically 35% hydrogen peroxide, 65% water, by weight in a liquid state).

A conventional VHP decontamination system for decontaminating an enclosure has a decontamination cycle comprised of four (4) basic operating phases, namely, (1) a dehumidification phase, (2) a conditioning phase, (3) a decontamination phase, and (4) an aeration phase. In the dehumidification phase the relative humidity within the enclosure is reduced by using a dryer. After the dehumidification phase is complete, the conditioning phase commences, wherein vaporized hydrogen peroxide is injected into the enclosure at a relatively high rate to bring the hydrogen peroxide concentration up to a desired level in a short period of time. After the conditioning phase, the decontamination phase is run where the injection rate may be modified to maintain the hydrogen peroxide vapor in the enclosure at a constant concentration level. In the aeration phase that follows the decontamination phase, the enclosure is aerated by stopping injection of the hydrogen peroxide vapor, and removing hydrogen peroxide vapor from the enclosure. A destroyer may be used to break down the hydrogen peroxide vapor into water and oxygen. Aeration continues until the concentration of hydrogen peroxide in the enclosure is below a threshold concentration level (e.g., 1 ppm).

Existing closed-loop VHP decontamination systems have a system airflow that is limited by the capacity of the dryer used therein. In this respect, if the airflow exceeds the dryer capacity, the air circulated therethrough is inadequately dehumidified. Where the VHP decontamination system is being used with a large enclosure, the limited dryer capacity can be particularly disadvantageous.

Some dryers have their own internal blowers that are continuously operated at full speed in order to quickly dehumidify a maximum volume of air. However, where the dryer having its own internal blower is a high capacity dryer, the airflow provided by the internal blowers may exceed the airflow rate suitable for certain operating phases of a VHP decontamination system (e.g., decontamination phase).

The present invention overcomes the foregoing problems, along with others, by providing a VHP decontamination system including an air bypass that allows efficient utilization of a high capacity dryer having a continuously operating internal blower.

SUMMARY OF THE INVENTION

In accordance with the present invention, there is provided a decontamination system for decontaminating an enclosure defining a region, the decontamination system comprising: a dryer; a dryer conduit, said dryer disposed in said dryer conduit, wherein said dryer conduit has an input side upstream of said dryer and an output side downstream of said dryer; a supply conduit in fluid communication with the output side of said dryer conduit and said region defined by the enclosure; a vaporizer disposed in said supply conduit for vaporizing a liquid decontaminant to produce vaporized decontaminant; a secondary supply conduit in fluidly connectable with the output side of said dryer conduit and said supply conduit; a return conduit in fluid communication with said region and the input side of said dryer conduit; a first valve means moveable between a first position and a second position, wherein said input side of said dryer conduit is in fluid communication with atmospheric air when the first valve means is in the first position; a second valve means moveable between a first position and a second position, wherein said output side of said dryer conduit is in fluid communication with atmosphere when said second valve means is in the first position, and said output side of said dryer conduit is in fluid communication with said secondary supply conduit when said second valve means is in the second position; and control means for controlling operation of said first and second valve means.

In accordance with another aspect of the present invention, there is provided a method for decontaminating a region defined by an enclosure using a vaporized decontaminant, the method comprising: circulating fluid from the region through a flow path to remove moisture therefrom, said flow path including a dryer conduit having a dryer disposed therein, said dryer conduit having an input side upstream of said dryer and an output side downstream of said dryer; putting the input side of the dryer conduit in fluid communication with atmospheric air and the output side of the dryer conduit in fluid communication with atmosphere, when the humidity within the region reaches a predetermined humidity level.

In accordance with still another aspect of the present invention, there is provided A decontamination system for decontaminating an enclosure defining a region, the decontamination system comprising: a circulation system in fluid communication with the region, said circulation system defining a closed loop fluid flow path to circulate fluid through the region; a bypass system in fluid communication with atmospheric air and the circulation system, said bypass system defining a bypass fluid flow path; and means for controlling the flow of atmospheric air through the bypass fluid flow path.

An advantage of the present invention is the provision of a VHP decontamination system that is adapted for efficient use of a high capacity air dryer.

Another advantage of the present invention is the provision of a VHP decontamination system that allows increased airflow through the system.

Still another advantage of the present invention is the provision of a VHP decontamination system that allows an increased dehumidification rate.

Still another advantage of the present invention is the provision of a VHP decontamination system that allows an increased aeration rate.

Yet another advantage of the present invention is the provision of a VHP decontamination system that regulates the use of available airflow capacity.

These and other advantages will become apparent from the following description of a preferred embodiment taken together with the accompanying drawings and the appended claims.

BRIEF DESCRIPTION OF THE DRAWING

The invention may take physical form in certain parts and arrangement of parts, a preferred embodiment of which will be described in detail in the specification and illustrated in the accompanying drawing which form a part hereof, and wherein the FIGURE is a schematic view of a vaporized hydrogen peroxide (VHP) decontamination system illustrating a preferred embodiment of the present invention.

DETAILED DESCRIPTION OF THE INVENTION

Referring now to the drawings wherein the showings are for the purposes of illustrating a preferred embodiment of the invention only and not for the purposes of limiting same, the FIGURE shows a vaporized hydrogen peroxide (VHP) decontamination system 10, illustrating a preferred embodiment of the present invention. System 10 is used with an enclosure 12 that defines an inner decontamination chamber or region 14. By way of example, and not limitation, enclosure 12 may take the form of an isolator, room or other sealed enclosure. The present invention is preferably used with regions or chambers having a volume of 300 cubic feet or smaller. However, it is contemplated that the present invention may also be used with larger regions or chambers. Articles to be decontaminated may be disposed within enclosure 12. Enclosure 12 includes an inlet port 20 and an outlet port 40.

System 10 includes a "closed loop" circulation system that is comprised of a plurality of conduits connected between inlet port 20 and outlet port 40 of enclosure 12. In the illustrated embodiment, the circulation system includes a supply conduit 22, a secondary supply conduit 24, a dryer conduit 32, and a return conduit 42. Supply conduit 22 is in fluid communication with dryer conduit 32 and region 14 via inlet port 20. Return conduit 42 is in fluid communication with dryer conduit 32 and region 14 via outlet port 40. A first end of dryer conduit 32 is in fluid communication with return conduit 42, as indicated above, while a second end of dryer conduit 32 terminates at a first port of a three-way bypass outlet valve 82. A second port of three-way bypass outlet valve 82 is connected with a first end of secondary supply conduit 24, and a third port of three-way bypass outlet valve 82 is connected with a first end of a bypass outlet conduit 38. A second end of secondary supply conduit 24 is in fluid communication with supply conduit 22. A second end of bypass outlet conduit 38 is in fluid communication with atmospheric air. The circulation system defines a primary fluid flow path "A" (indicated by the solid arrows) and secondary fluid flow path "B" (indicated by the short dashed arrows), as will be described in further detail below.

In the illustrated embodiment, bypass outlet valve 82 has only two positions. In a first position, bypass outlet valve 82 puts second end of dryer conduit 32 in fluid communication with secondary supply conduit 24. In a second position, bypass outlet valve 82 puts second end of dryer conduit in fluid communication with bypass outlet conduit 38.

A bypass inlet conduit 36 has a first end in fluid communication with dryer conduit 32 and return conduit 42, and a second end in fluid communication with atmospheric air. A bypass inlet valve 72 is disposed in bypass inlet conduit 36 to control the flow of atmospheric air through bypass inlet conduit 36.

System 10 includes a bypass system that is comprised of a plurality of conduits that are in fluid communication with the atmosphere and the circulation system described above. In the illustrated embodiment, bypass system includes bypass inlet conduit 36, dryer conduit 32 and bypass outlet conduit 38. The bypass system defines a bypass fluid flow path "C" (indicated by the long dashed arrows), as will be described in further detail below.

A vaporizer 130 is disposed in supply conduit 22. Vaporizer 130 includes a vaporization chamber (not shown), wherein a liquid decontaminant is heated to form a gaseous or vaporized decontaminant. A feed conduit 52 connects a liquid decontaminant supply 160 with vaporizer 130. Decontaminant supply 160 may include a replaceable cartridge. A conventionally known balance device (not shown) may also be associated with decontaminant supply 160, to measure the actual mass of liquid decontaminant being supplied to vaporizer 130. A typical decontaminant is an aqueous solution of hydrogen peroxide comprised of about 35% by weight hydrogen peroxide and about 65% by weight water.

In accordance with the illustrated embodiment, vaporizer 130 includes an internal heater (not shown), a thermal cutoff or over-temperature switch (not shown), and a temperature sensor 144. The internal heater of vaporizer 130 heats the liquid decontaminant supplied by decontaminant supply 160, thereby vaporizing the decontaminant by conventionally known means. In the illustrated embodiment, the liquid decontaminant is an aqueous solution of hydrogen peroxide. The vaporized hydrogen peroxide produced by vaporizer 130 is supplied to region 14 of enclosure 12 via supply conduit 22. The thermal cutoff or over-temperature switch of vaporizer 130 automatically cuts power to the vaporizer heater in the event that a predetermined temperature limit has been exceeded. Temperature sensor 144 provides a signal indicative of the temperature of the fluid inside the vaporization chamber of vaporizer 130.

An injection pump 170 driven by a motor 172 is provided to convey metered amounts of the liquid decontaminant to vaporizer 130. In an alternative embodiment, pump 170 is provided with an encoder (not shown) that allows monitoring of the amount of decontaminant being metered to vaporizer 130. If an encoder is provided with pump 170, a balance device for decontaminant supply 160 is not required.

A filter 176 is provided in feed conduit 52 to filter the liquid decontaminant before it is received by vaporizer 130. A pressure switch 174 is also provided in feed conduit 52. Pressure switch 174 is operable to provide an electrical signal in the event that a certain static head pressure does not exist in feed conduit 52.

An injection blower 110 and an air preheater 120 are located within supply conduit 22, upstream from vaporizer 130. Injection blower 110, driven by a motor 112, is disposed within supply conduit 22 between vaporizer 130 and dryer conduit 32. Blower 110 is operable to circulate fluid through supply conduit 22. Air preheater 120 is disposed within supply conduit 22 between blower 110 and vaporizer 130. Air preheater 120 heats the fluid passing therethrough. A thermal cutoff or over-temperature switch (not shown) automatically cuts power to heater 120 in the event that a predetermined temperature limit has been exceeded. A temperature sensor 124 provides a signal indicative of the temperature of the fluid inside air preheater 120.

A flow sensor 150 and a high efficiency particulate air (HEPA) filter 152 are located within supply conduit 22, downstream from vaporizer 130. Flow sensor 150 is disposed in supply conduit 22 between vaporizer 130 and enclosure 12. Flow sensor 150 provides a signal indicative of the fluid flow rate through supply conduit 22. A temperature sensor 148 is located in supply conduit 22 proximate to flow sensor 150 to provide a signal indicative of the temperature of the fluid flowing through supply conduit 22. Filter 152 is disposed within supply conduit 22 between flow sensor 150 and enclosure 12. Fluid is filtered by filter 152 before entering region 14 of enclosure 12.

In the illustrated embodiment, a chemical agent conduit 54 connects a chemical agent supply 180 to supply conduit 22, between flow sensor 150 and filter 152. A valve 192 is disposed within chemical agent conduit 54 to control the flow of chemical agent (e.g., ammonia) from chemical agent supply 180 to supply conduit 22.

Referring now to return conduit 42, a circulation blower 66, driven by a motor 68, is disposed within return conduit 42 between enclosure 12 and dryer conduit 32. Circulation blower 66 is operable to circulate fluid through return conduit 42. A catalytic destroyer 60 is disposed in return conduit 42 between blower 66 and enclosure 12. Catalytic destroyer 60 is operable to destroy hydrogen peroxide flowing therethrough, by converting hydrogen peroxide into water and oxygen, as is conventionally known.

In the illustrated embodiment, a HEPA filter 62 is preferably disposed between destroyer 60 and enclosure 12, and a carbon filter 64 is disposed between blower 66 and destroyer 60. Carbon filter 64 used to filter chemical agents from the fluid stream.

A dryer 90 is disposed within dryer conduit 32 to remove moisture from the fluid blown through dryer conduit 32. Accordingly, dryer conduit 32 has an input side that is upstream of dryer 90 and an output side that is downstream of dryer 90. Dryer 90 is preferably a conventionally known regenerative desiccant dryer that collects water vapor from the fluid stream passing therethrough. Regenerative desiccant dryers use a desiccant (e.g., silica gel, activated alumina and molecular sieve), which adsorbs water vapor in the fluid stream. It should be understood that dryer 90 may take other forms including a refrigerated dryer. In the illustrated embodiment, dryer 90 also includes a high-volume internal blower 100, driven by a motor 102. Dryer 90 may also be put in fluid connection with a regeneration unit (not shown) via a regeneration conduit 48. The regeneration unit regenerates the desiccant by driving off moisture in a regeneration process that includes applying dry, expanded purge air, heat, or a combination of both. By way of example, and not limitation, dryer 90 may have a drying capacity (i.e., maximum volume of air through the dryer per unit time) in the range of 120 to 6000 cubic meters of air per hour. Motor 102 may have a horsepower in the range of 1 to 20 hp (i.e., dryer "size"). Examples of suitable desiccant and refrigerated dryers include, by are not limited to, dryer model nos. MG90, MG150 and HCD-4500, from Munters of the United Kingdom.

A concentration sensor 15, a pressure sensor 16, and a humidity sensor 18 are located inside region 14 of enclosure 12. Concentration sensor 15 provides a signal indicative of the concentration of hydrogen peroxide in region 14. Pressure sensor 16 provides a signal indicative of the pressure level within region 14. Humidity sensor 18 provides a signal indicative of the humidity level within region 14.

As discussed above, a "closed loop" circulation system defines a primary fluid flow path "A" and secondary fluid flow path "B." Primary fluid flow path "A" is defined from vaporizer 130 through supply conduit 22 to region 14, through return conduit 42 to destroyer 60 and dryer conduit 32, through dryer conduit 32 to dryer 90, and to air preheater 120 and vaporizer 130 through supply conduit 22. Secondary fluid flow path "B" is defined from dryer conduit 32 (at outlet of dryer 90) through secondary supply conduit 24. In this respect, vaporizer 130 and air preheater 120 along supply conduit 22 are bypassed in secondary fluid flow path "B."

As noted above, the bypass system defines a bypass fluid flow path "C." Bypass fluid flow path "C" is defined by bypass inlet conduit 36, through dryer conduit 32 to dryer 90, and continuing through dryer conduit 32 and bypass outlet conduit 38 to atmosphere.

A control system 200 controls operation of VHP decontamination system 10. Control system 200 includes a controller 202 that preferably takes the form of a conventional microcontroller or microcomputer. Vaporizer 130; motors 68, 112, 172; heater 120 and the internal heater of vaporizer 130; and valves 72, 82, 192, are controlled by control signals transmitted by controller 202. Controller 202 receives data signals from flow sensor 150; temperature sensors 124, 144, 148; concentration sensor 15; pressure sensor 16; humidity sensor 18; and pressure switch 174.

The present invention shall now be further described with reference to the operation of VHP decontamination system 10. VHP decontamination system 10 has four (4) basic operating phases, namely, a dehumidification phase, a conditioning phase, a decontamination phase, and an aeration phase. In the dehumidification phase the relative humidity within region 14 of enclosure 12 is reduced by using dryer 90 to remove water vapor therefrom. After the dehumidification phase is completed, the conditioning phase commences, wherein liquid decontaminant (i.e., an aqueous solution of hydrogen peroxide) is vaporized by vaporizer 130 and injected into region 14 at a relatively high rate to rapidly increase the concentration of hydrogen peroxide inside region 14. Following the conditioning phase, the decontamination phase commences wherein the decontaminant injection rate is regulated to maintain the hydrogen peroxide concentration inside region 14 at a desired constant concentration level In the aeration phase that follows the decontamination phase, enclosure 12 is aerated by stopping injection of the vaporized hydrogen peroxide into region 14, and removing hydrogen peroxide therefrom. Aeration continues until the hydrogen peroxide concentration level in region 14 is below an allowable threshold concentration level (e.g., 1 ppm).

Initially, controller 202 transmits control signals to turn off motors 68, 110 and 172. Accordingly, circulation blower 66, injection blower 110 and injection pump 170 are inactive. Controller 202 transmits a first control signal to move bypass inlet valve 72 to a closed position (thereby preventing atmospheric air from entering system 10), and a second valve control signal to move bypass outlet valve 82 to a position wherein dryer conduit 32 is in fluid communication with secondary supply conduit 24. It should be understood that in the illustrated embodiment of the present invention, motor 102 of internal blower 100 (associated with dryer 90) remains active throughout all four (4) of the operating phases of VHP decontamination system 10, described in detail below. The continuous activation of motor 102 of internal blower 100, prevents overheating of the desiccant of dryer 90.

As indicated above, a typical decontamination cycle includes a dehumidification phase, a conditioning phase, a decontamination phase and an aeration phase. Each of these operating phases will now be described in detail.

Dehumidification Phase

When the dehumidification phase is first initiated, controller 202 transmits control signals to turn on heater 120 and the internal heater of vaporizer 130, and to activate motors 68, 112. Accordingly, circulation blower 66 and injection blower 110 are activated. As indicated above, bypass inlet valve 72 is in the closed position, and bypass outlet valve 82 is in a position wherein dryer conduit 32 is in fluid communication with secondary supply conduit 24. Consequently, circulation blower 66 and injection blower 110 cause fluid circulation through "closed loop" fluid flow paths "A" and "B," thereby rapidly dehumidifying region 14. In this regard, air drawn out of region or enclosure 14 by circulation blower 66 is conveyed through dryer 90 to remove moisture therefrom. Dehumidified air exiting dryer 90 is drawn into supply conduit 22 by injection blower 110. Prior to injection into region 14, air preheater 120 and the internal heater of vaporizer 130 heat the dehumidified air stream as it travels through supply conduit 22. Additional dehumidified air follows secondary flow path "B."

As indicated above, humidity sensor 18 located inside region 14 provides a signal to controller 202 indicative of the humidity level inside region 14. When controller 202 determines that the desired humidity level in region 14 has been reached, controller 202 transmits a control signal to open bypass inlet valve 72, thereby allowing atmospheric air to be drawn into bypass inlet conduit 36, and through dryer 90. At this time, controller 202 also transmits a control signal to the bypass outlet valve 82 to move bypass outlet valve 82 to a position, wherein dryer conduit 32 is in fluid communication with the atmosphere via bypass outlet conduit 38. As a result, fluid flow along flow path "B" ends and fluid flow along bypass flow path "C" commences. Accordingly, some fluid traveling through dryer conduit 32 will be directed to the atmosphere through bypass outlet conduit 38. It should be understood that fluid flow continues along flow path "A" since injection blower 110 and circulation blower 66 remain active.

Conditioning Phase

The conditioning phase follows the dehumidification phase described above. Bypass inlet valve 72 remains open and bypass outlet valve 82 remains in a position wherein dryer conduit 32 is in fluid communication with the atmosphere via bypass outlet conduit 38. Accordingly, fluid flow continues along bypass flow path "C." Controller 202 transmits control signals to motor 68 (associated with circulation blower 66) to maintain a predetermined pressure level (positive or negative) within region 14, as indicated by pressure sensor 16. Controller 202 also transmits a control signal to motor 112 (associated with injection blower 110) to maintain a predetermined fluid flow through supply conduit 22, based upon feedback data received by controller 202 from flow sensor 150. Therefore, fluid flow also continues along flow path "A."

Since bypass outlet valve 82 remains in a position wherein dryer conduit 32 is in fluid communication with the atmosphere via bypass outlet conduit 38, injection blower 110 will draw only the amount of air from the outlet of dryer 90 that is required to maintain the predetermined fluid flow through supply conduit 22. In this respect, excess air that is output from dryer 90 exits system 10 to the atmosphere via bypass outlet conduit 38. Filters 62 and 64, and destroyer 60 operate to ensure that no biological, chemical, or hydrogen peroxide exit to the atmosphere via bypass outlet conduit 38.

Heater 120 and the internal heater of vaporizer 130 also remain turned on during the conditioning phase. Controller 202 activates injection pump 170 by transmitting control signals to motor 172. Injection pump 170 supplies metered amounts of liquid hydrogen peroxide to vaporizer 130. The liquid hydrogen peroxide is vaporized in vaporizer 130 in a conventionally known manner. The vaporized hydrogen peroxide is injected into region 14 via supply conduit 22 at a relatively high rate to rapidly increase the concentration of hydrogen peroxide inside region 14 to a desired level suitable for a decontamination operation.

Decontamination Phase

Once the hydrogen peroxide has reached the desired concentration level within region 14, the decontamination phase may commence. In the decontamination phase, VHP decontamination system 10 continues to generally operate in the same manner described above for the conditioning phase. Thus, there is fluid flow along flow paths "A" and "C." However, controller 202 modifies the speed of motor 172 associated with injection pump 170 in order to maintain a generally constant concentration of hydrogen peroxide in region 14 that is suitable for decontamination.

If an additional chemical agent (e.g., ammonia) is to be injected into region 14 during the decontamination phase, controller 202 transmits control signals to move valve 192 to an open position until the desired concentration of the chemical agent is reached in region 14 for a predetermined period of time. Controller 202 may cycle valve 192 between the open and closed positions, as necessary, to maintain the desired concentration of the chemical agent.

The decontamination phase is run for a predetermined period of time, preferably with the concentration level of the vaporized hydrogen peroxide in region 14 remaining at a generally constant level, for a predetermined period of time that is sufficient to effect the desired decontamination.

Aeration Phase

As indicated above, the aeration phase follows the decontamination phase. After the decontamination phase is completed, controller 202 transmits a control signal to turn off motor 172 associated with injection pump 170, thereby shutting off the flow of liquid hydrogen peroxide to vaporizer 130. Controller 202 also transmits a control signal to close bypass inlet valve 72 to prevent atmospheric air from being drawn into VHP decontamination system 10 via bypass inlet conduit 36. In addition, controller 202 transmits a control signal to bypass outlet valve 82 to move bypass outlet valve 82 to a position wherein dryer conduit 32 is in fluid communication with secondary supply conduit 24, thereby directing fluid flow from dryer 90 into region 14. Accordingly, fluid flow along bypass flow path "C" ends, and fluid flow along flow path "B" commences.

In the aeration phase, controller 202 transmits control signals to motor 68 to operate circulation blower 66 at or near full speed. Injection blower 110 may also be active during the aeration phase. Thus, fluid circulates along flow paths "A" and "B" during the aeration phase.

Hydrogen peroxide vapor withdrawn from region 14 by blower 66 is broken down into water and oxygen by destroyer 60. As a result, the concentration of hydrogen peroxide in region 14 of enclosure 12 is reduced below a threshold level (e.g., 1 ppm).

A decontamination cycle is complete following the aeration phase. A subsequent decontamination cycle commences with a dehumidification phase, as described above.

Other modifications and alterations will occur to others upon their reading and understanding of the specification. It is intended that all such modifications and alterations be included insofar as they come within the scope of the invention as claimed or the equivalents thereof.

The invention claimed is:

1. A decontamination system for decontaminating an enclosure defining a region, the decontamination system comprising:
   a dryer;
   a dryer conduit, said dryer disposed in said dryer conduit, wherein said dryer conduit has an input side upstream of said dryer and an output side downstream of said dryer;
   a supply conduit connected at one end to the output side of said dryer conduit and at another end to said region defined by the enclosure;
   a vaporizer disposed in said supply conduit for vaporizing a liquid decontaminant to produce vaporized decontaminant;
   a secondary supply conduit connected at one end to the output side of said dryer conduit and at another end to said supply conduit downstream of said vaporizer disposed therein;
   a return conduit connected at one end to said region and at another end to the input side of said dryer conduit;
   a bypass inlet conduit connected at one end to the input side of said dryer conduit and said return conduit and fluidly communicating with atmospheric air at another end;
   a bypass outlet conduit connected at one end to the outlet side of said dryer and to said secondary supply conduit and fluidly communicating with atmospheric air at another end;
   a first valve disposed in said bypass inlet conduit, said first valve moveable between a first position and a second position, wherein said input side of said dryer conduit is in fluid communication with atmospheric air and said return conduit when the first valve is in the first position and said input side of said dryer conduit is not in fluid communication with atmospheric air when the first valve is in the second position;
   a second valve disposed at an intersection of said dryer conduit, said secondary supply conduit and said bypass outlet conduit, said second valve moveable between a first position and a second position, wherein said output side of said dryer conduit is in fluid communication with atmospheric air and not in fluid communication with said secondary supply conduit, when said second valve is in the first position, and said output side of said dryer conduit is in fluid communication with said secondary supply conduit and not in fluid communication with the atmospheric air, when said second valve is in the second position; and
   control means for controlling operation of said first and second valves.

2. A decontamination system according to claim 1, wherein said decontamination system includes an injection blower disposed within said supply conduit for injecting the vaporized decontaminant into the region.

3. A decontamination system according to claim 1, wherein said decontamination system includes a circulation blower disposed within said return conduit, said circulation blower drawing fluid from the enclosure into the return conduit.

4. A decontamination system according to claim 1, wherein said decontamination system includes a destroyer disposed within said return conduit.

5. A decontamination system according to claim 1, wherein said decontamination system includes a destroyer disposed within said return conduit.

6. A decontamination system according to claim 1, wherein said decontamination system includes a pump for supplying liquid decontaminant to said vaporizer.

7. A decontamination system according to claim 1, wherein said decontamination system includes a flow sensor disposed within said supply conduit to sense a fluid flow rate.

8. A decontamination system according to claim 1, wherein said decontamination system includes a flow sensor disposed within said supply conduit to sense a fluid flow rate.

9. A decontamination system according to claim 1, wherein said decontamination system includes a pressure sensor disposed within said enclosure, said pressure sensor providing a signal to the control means indicative of the pressure within the region.

10. A decontamination system according to claim 1, wherein said decontamination system includes a humidity sensor disposed within said enclosure, said humidity sensor providing a signal to the control; means indicative of the humidity within the region.

11. A decontamination system according to claim 1, wherein said secondary supply conduit is fluidly connectable with said supply conduit between said vaporizer and said region defined by the enclosure.

12. A decontamination system for decontaminating an enclosure defining a region, the decontamination system comprising:
    a circulation system in fluid communication with the region, said circulation system defining a closed loop fluid flow path to circulate fluid through the region;
    a bypass system in fluid communication with atmospheric air and the circulation system, said bypass system defining a bypass fluid flow path, said bypass system including a bypass inlet conduit and a bypass outlet conduit;
    a dryer conduit having a dryer disposed therein, said dryer conduit having an input side upstream of said dryer and an output side downstream of said dryer, said input side of said dryer conduit connected to said bypass inlet conduit and said output side of said dryer conduit connected to said bypass outlet conduit;
    a supply conduit having a vaporizer disposed therein for vaporizing a liquid decontaminant to produce a vaporized decontaminant, said supply conduit connected to the output side of said dryer conduit and said region defined by the enclosure;
    a secondary supply conduit connected to the output side of said dryer conduit, said bypass outlet conduit and with said supply conduit downstream of said vaporizer disposed therein;
    a return conduit connected to said region, the input side of said dryer conduit and said bypass inlet conduit;
    a valve disposed at an intersection of said dryer conduit, said bypass outlet conduit and said secondary supply conduit, said valve responsive to said control means to move between a first position and a second position, wherein said output side of dryer conduit is in fluid communication with atmosphere and not in fluid communication with said secondary supply conduit, when said valve is in the first position, and said output side of said dryer conduit is in fluid communication with said secondary supply conduit and not in fluid communication with the atmosphere, when said valve is in the second position; and control means operable in a first mode wherein a fluid flow path is established between the dryer conduit, said return conduit and atmosphere and a fluid flow path is terminated between the dryer conduit and the secondary supply conduit, and operable in a second mode wherein a fluid flow path is terminated between the dryer conduit and atmosphere and a fluid flow path is established between the dryer conduit and the secondary supply conduit.

13. A decontamination system according to claim 12, wherein said decontamination system further comprises:

a second valve disposed in said bypass inlet conduit, said valve responsive to said control means to move between a first position and a second position, wherein said input side of said dryer conduit is in fluid communication with atmospheric air when the second valve is in the first position and said input side of said dryer is in fluid communication with said return conduit when said valve is in both the first position and the second position.

14. A decontamination system according to claim 12, wherein said decontamination system includes an injection blower disposed within said supply conduit for injecting the vaporized decontaminant into the region.

15. A decontamination system according to claim 12, wherein said decontamination system includes a circulation blower disposed within said return conduit, said circulation blower drawing fluid from the enclosure into the return conduit.

16. A decontamination system according to claim 12, wherein said dryer includes an internal blower.

17. A decontamination system according to claim 12, wherein said decontamination system includes a destroyer disposed within said return conduit.

18. A decontamination system according to claim 12, wherein said liquid decontaminant is an aqueous solution of hydrogen peroxide.

19. A decontamination system according to claim 12, wherein said decontamination system includes a flow sensor disposed within said supply conduit to sense a fluid flow rate.

20. A decontamination system according to claim 12, wherein said decontamination system includes a flow sensor disposed within said supply conduit to sense a fluid flow rate.

21. A decontamination system according to claim 12, wherein said decontamination system includes a pressure sensor disposed within said enclosure, said pressure sensor providing a signal to the control means indicative of the pressure within the region.

22. A decontamination system according to claim 12, wherein said decontamination system includes a humidity sensor disposed within said enclosure, said humidity sensor providing a signal to the control means indicative of the humidity within the region.

23. A decontamination system according to claim 12, wherein said secondary supply conduit is fluidly connectable with said supply conduit between said vaporizer and said region defined by the enclosure.

* * * * *